(12) United States Patent
Ihlefeld et al.

(10) Patent No.: US 8,675,195 B2
(45) Date of Patent: Mar. 18, 2014

(54) DEVICE FOR DETERMINING PARTICLE SIZES

(75) Inventors: Joachim Ihlefeld, Dresden (DE); Amer Tarraf, Kreuzlingen (CH)

(73) Assignee: Baumer Optronic GmbH, Radeberg (DE)

( * ) Notice: Subject to any disclaimer, the term of this patent is extended or adjusted under 35 U.S.C. 154(b) by 258 days.

(21) Appl. No.: 13/257,079

(22) PCT Filed: Mar. 23, 2010

(86) PCT No.: PCT/EP2010/001798
§ 371 (c)(1),
(2), (4) Date: Sep. 16, 2011

(87) PCT Pub. No.: WO2010/108648
PCT Pub. Date: Sep. 30, 2010

(65) Prior Publication Data
US 2012/0008143 A1    Jan. 12, 2012

(30) Foreign Application Priority Data
Mar. 23, 2009  (DE) .................... 10 2009 014 080

(51) Int. Cl.
*G01N 15/02*     (2006.01)
(52) U.S. Cl.
USPC ........... 356/335; 356/336; 356/337; 356/338; 356/339
(58) Field of Classification Search
USPC ......................................... 356/335
See application file for complete search history.

(56) References Cited

U.S. PATENT DOCUMENTS

| 5,327,217 | A  |   | 7/1994 | Kanai et al. |
|-----------|----|---|--------|--------------|
| 5,548,395 | A  |   | 8/1996 | Kosaka |
| 5,748,305 | A  | * | 5/1998 | Shimono et al. ........... 356/237.2 |
| 6,115,119 | A  |   | 9/2000 | Sieracki et al. |
| 6,525,325 | B1 |   | 2/2003 | Andrews et al. |
| 7,737,088 | B1 | * | 6/2010 | Stähler et al. .................. 506/30 |
| 2008/0231854 | A1 |   | 9/2008 | Seifert et al. |

FOREIGN PATENT DOCUMENTS

| DE | 697 30 632 T2 | 2/2005 |
| GB | 2 203 542 A | 10/1988 |
| JP | 2003 057164 A | 2/2003 |
| JP | 2006 170910 A | 6/2006 |

\* cited by examiner

*Primary Examiner* — Tarifur Chowdhury
*Assistant Examiner* — Omar Nixon
(74) *Attorney, Agent, or Firm* — McGlew and Tuttle, P.C.

(57) ABSTRACT

A device and process for determining sizes of particles of a particle stream. A first optical measuring system with a first dot matrix sensor and a lighting device, which transilluminates the measuring volume are provided. The first dot matrix sensor and the lighting device form a transmitted-light arrangement. The computing device determines projection areas of particles within the transilluminated measuring volume from the image data of the first dot matrix sensor. The optical measuring arrangement includes a second optical measuring system with a second dot matrix sensor for detecting the diffraction pattern of the particles. The computing device determines a size distribution of the particles in the measuring volume based on the projection areas and the diffraction pattern. The computing device forms the size distribution from particle sizes determined on the basis of the projection areas and from particle sizes determined on the basis of the diffraction pattern.

19 Claims, 5 Drawing Sheets

DEVICE FOR DETERMINING PARTICLE SIZES

CROSS REFERENCE TO RELATED APPLICATIONS

This application is a United States National Phase application of International Application PCT/EP2010/001798 and claims the benefit of priority under 35 U.S.C. §119 of German Patent Application DE 10 2009 014 080.8 filed Mar. 23, 2009, the entire contents of which are incorporated herein by reference.

FIELD OF THE INVENTION

The present invention pertains, in general, to the determination of particle sizes. The present invention pertains, in particular, to the determination of the sizes of particles of a particle stream.

BACKGROUND OF THE INVENTION

A device for measuring particle size distributions is known from GB 2 203 542 A. The measurement of particle sizes of a particle stream of low concentration is carried out by forward light scattering on the basis of recorded Fraunhofer diffraction patterns. A high-intensity light source, e.g., a pulsed gallium arsenide laser, is needed for the process. Due to the high-intensity light source, a blocker is used to block the non-scattered light or the light scattered in the forward direction.

This special device shall make it possible to detect very small particles of sizes smaller than 1 μm in diameter even at low concentrations.

Such particles have sizes on the order of magnitude of the wavelength of the light being used. If the particles become markedly larger than the wavelength of the light, an analysis of the diffraction pattern may, however, lead to misinterpretations, especially if the particle has a shape markedly differing from the spherical shape. The diffraction thus becomes more complex, which cannot now be unambiguously discriminated, among other things, from an intensity distribution from a superposition of several separate particles. In addition, the problem is that a diffraction measurement is unable to distinguish agglomerated small particles from an individual, larger particle.

Since the process described in GB 2 203 542 A is not well suited for large particles, the problem is that very broad size distributions must be detected correctly.

SUMMARY OF THE INVENTION

Ae basic object of the present invention is therefore to make possible, likewise optically, the detection of the sizes of particles within a large measuring range, where the particle sizes may differ from each other by several orders of magnitude.

Accordingly, the present invention provides for a device for determining particle sizes of particle streams, which flow through a measuring volume and an optical measuring arrangement detecting the measuring volume and a computing means connected to the optical measuring arrangement, wherein the optical measuring arrangement comprises
 a first, preferably telecentric optical measuring system with
  a first dot matrix sensor and
  a lighting means, wherein
   the lighting means transilluminates the measuring volume, and
   the first dot matrix sensor and the lighting means form a transmitted-light device, and wherein
  the computing means is set up to determine projection areas of particles within the transilluminated measuring volume from the image data of the first dot matrix sensor,
and wherein the optical measuring device comprises a second optical measuring system with a second dot matrix sensor for detecting the diffraction pattern of the particles,
and wherein the computing means is set up to determine a size distribution of the particles in the measuring volume on the basis of the projection areas and the diffraction pattern, wherein the computing means is set up to form the size distribution from particle sizes determined on the basis of the projection areas, on the one hand, and particle sizes determined on the basis of the diffraction pattern, on the other hand, and especially to also compose a common distribution from the two distributions.

A corresponding process for determining particle size distributions of particle streams, especially by means of a device according to the present invention, is correspondingly based on the fact that
 a measuring volume is transilluminated with a lighting means by means of a first, preferably telecentric optical measuring system and
 the transmitted light signal is detected by a first dot matrix sensor of the first optical measuring system, wherein
 projection areas of particles are determined on the basis of the transmitted light signal by means of a computing means, and wherein a diffraction pattern of the particles is determined by means of a second dot matrix sensor of a second optical measuring system of the optical measuring arrangement, and wherein the size distribution is formed by means of the computing means from particle sizes determined on the basis of the projection areas, on the one hand, and particle sizes determined on the basis of the diffraction pattern, on the other hand. In a variant of the present invention, contour dots are determined to determine the projection areas of particles and subsequently segmented into contours or connected to form contours. To recognize a particle and to determine the projection area thereof, contour segments can be sought for this, which yield closed bordering curves. Based on these curves, the inner area of the curve, which represents the projection area of the corresponding particle, can then be determined. The recognition of the inner area can be determined very simply, for example, on the basis of the image brightness values, because the inner area is typically darker than the surroundings in a transmitted-light image. The determination of the contour dots on the basis of the gray scale value over the edge of the projection area of a particle can be performed to the subpixel accuracy if a plurality of dots are included in the calculation of the contour dot location.

To obtain a contiguous size distribution over a broad range, the size distribution determined on the basis of the diffraction pattern can be calibrated by the computing means by means of an area, overlapping with this size distribution, of the other size distribution determined on the basis of the projection areas or scaled to this size distribution. Accordingly, it is generally favorable if the measuring ranges of the two optical measuring systems partly overlap, and the overlap is meaningfully located in the range of small particle sizes of the distribution obtained by area projection and in the range of large particle sizes of the broader distribution determined on the basis of the diffraction pattern.

In a preferred variant of the present invention, the measuring volume is a tube through which the particle stream to be analyzed flows. This may be transparent or have window areas in order to let through the light for the measurements.

Consequently a measurement of projection areas, which measurement is well suited for larger particles, is combined with a measurement of diffraction patterns, which measurement is well suited for small particles.

The two size-measuring ranges of the optical measuring systems can be divided on the basis of predetermined area threshold values for the projection areas that can be assigned to the particles. Threshold values that divide the measuring ranges may also be defined in another manner. At any rate, the threshold values can be assigned to certain sizes of projection areas.

According to another aspect of the present invention, a device for determining particle sizes is provided for the analysis of particle streams in a transparent measuring volume, wherein the geometric dimension of the smallest particles to be measured is preferably smaller than or equal to the depth of field range of an optical measuring system, which range is determined by the largest particles to be measured, and wherein projection areas of particles are detected with a first telecentric optical measuring system at discrete points in time within a measuring range beginning from a first area threshold value and/or contrast threshold value and integral spectra are measured with a second, diffractive optical measuring system within a time window below a second area threshold value, wherein the area threshold values are approximately equal; or overlap to form a common range.

A high depth of field range of the first optical measuring system or a possibly depth-independent imaging during the projection area measurement is, in general, advantageous for making it possible to correctly measure the projection areas in a sufficiently large measuring volume. Telecentric lighting means and/or lenses are therefore especially advantageous. Homogenous illumination of the measuring area is especially advantageous concerning the lighting.

It is also favorable to design the second optical measuring system as a transmitted-light arrangement. A coherent light source, especially a laser, is preferred as a lighting source for the second optical measuring system. However, the use of a white light source or a plurality of coherent light sources was also considered as an alternative in order to further improve the detection of the particle sizes on the basis of the color temperature-dependent, different diffractions.

Since the first optical measuring system is designed for the detection of larger particles and the second optical measuring system for the detection of smaller particles, it is, furthermore, favorable if the first optical measuring system and the second optical measuring system have different size-measuring ranges or imaging scales, wherein the second, diffractive optical measuring system has an imaging scale that is at least twice as high and preferably at least 5 times as high as the imaging scale of the first optical measuring system.

Unlike prior-art, diffractively operating particle analyzers, the device may advantageously also be used to determine velocity distributions of the particle stream and/or to determine flows determined from the velocities. The first optical measuring system is set up for this to record at least two images one after another, and the computing means is set up to calculate the change in location in the two images for particles with the size of the area projection above an area threshold value and to determine a velocity distribution as a function of the distance difference of the particle location and the particle size.

Furthermore, the computing means may be set up to correlate the remaining gray scale value between the two images, while excluding particles with the size of the area projection above an area threshold value, to determine the corresponding shift vector on the basis of this correlation, and to calculate a mean velocity for small particles with an area projection below the area threshold value. It is thus surprisingly possible to determine even velocity values of particles that are not even resolved by the first optical measuring system any more.

A uniform velocity model can be composed from the two measurements by the computing means. A data structure with particle histograms and location- and size-dependent measured velocity data and/or a particle size histogram corrected with detection probability and/or other variables, e.g., a determined particle velocity, can be determined for this, preferably in the form of a projection area histogram.

It frequently happens, precisely in case of broad particle size distributions, that the broad distribution is formed or caused by particles of different kinds, e.g., particles formed from different materials. Particular substances are often not homogeneous concerning the particle composition or shape. It may be desirable in this case to obtain more information on the particle stream, which goes beyond a mere size distribution. In a variant of the present invention, an additional multicolor, preferably white incident-light lighting means of the first optical measuring system is provided for this, besides the transmitted-light lighting means. The transmitted-light arrangement is especially suitable for the determination of sizes, because the projection area of a particle illuminated in transmitted light is independent from the material, color or texture of the particle. By contrast, additional information can be obtained concerning the color of the particle with a multicolor, especially white incident-light lighting means. The color can then be used in most cases for the identification or classification of the particles in case of particle mixtures that are inhomogeneous in respect to the material. A particle stream of an abrasive, e.g., for sandblasting or polishing, shall be mentioned as an example. The particle stream will also contain abraded particles from the material removed besides the abrasive particles. These kinds of particles will typically also differ in terms of their color, besides in terms of their size. To make it possible to make such a discrimination in terms of color, the dot matrix sensor of the first optical measuring system is preferably designed as a color sensor. the color information can then be used by the computing means to assign the color information to particles and to calculate a particle size distribution, which contains as another attribute the particle color or a parameter associated with the color, such as the kind of particle. Particle size distributions can now be generated, in particular, for particles of a certain color or particle type.

The incident light is preferably arranged such that its light illuminates the particles at an angle of preferably 45° and more in relation to the optical axis. In particular, the light source is collimated now such that its light beam passes completely by an opposite lens of the transmitted-light lighting means or at least passes completely through the optical axis before falling on the lens. Interfering signals due to reflections of the lens of the transmitted-light lighting means are thus avoided.

The color analysis is preferably performed directly on the basis of a Bayer pattern. Conversion to actual tristimulus values of the pixels is thus eliminated. The computing effort can be further reduced considerably if the computing means determines at first contours belonging to particles and then performs a color analysis selectively within the contours belonging to the particles. The computation time for determining color attributes can thus be reduced by 95% or more compared to a full-area color analysis.

A lower spatial resolution is needed per se in case of a color analysis than for the determination of the contours of the particles in the transmitted-light measurement. On the other hand, a great depth of field, which can be obtained with a small aperture, is desirable for the latter measurement. It would therefore be desirable for an optimization of the measurements to have a first optical measuring system whose camera can be operated simultaneously with different apertures.

The following principle is suitable for this: A lens diaphragm of the camera is used, which is designed as a polarizer with an aperture opening. The light of a first lighting means, for which a small diaphragm is desired, is polarized linearly such that it does not enter the polarizer. In other words, the polarizer is in blocking orientation against the polarization plane of the light. The second lighting means is unpolarized or is polarized in the transmission direction. The light of the first lighting means thus falls only through the aperture opening. The light of the second lighting means is, by contrast, also let through the polarizer.

Such an arrangement can be used highly advantageously for other optical detection means as well. Applications of a diaphragm according to the present invention arise, for example, wherever weak, unpolarized secondary signals are generated. One example of this is represented by fluorescence images. A lighting means polarized in the blocking direction would then be needed for this. The weak fluorescent light generated by the lighting means can then pass through the polarization filter at a rate of 50%, so that an essentially larger diaphragm is available for this light.

Accordingly, the present invention provides, in another aspect, without limitation to a device for determining particle sizes, for an optical measuring device, which comprises a camera with dot matrix sensor with a lens arranged in front of it, as well as a lighting means, wherein said lighting means emits linearly polarized light and wherein the lens of the camera comprises a diaphragm in the form of a polarization filter with an aperture opening arranged therein, and wherein the light source and the polarization filter are arranged such that the polarization plane of the light and the transmission direction of the polarizer are crossed in relation to one another. Concerning the device according to the present invention for determining particle sizes, the lighting means, which forms a transmitted-light arrangement with the sensor, is designed as a linearly polarized lighting means. A lens with diaphragm, which is designed, as was mentioned, in the form of a polarization filter arranged crossed in relation to the polarization plane with an aperture opening arranged therein, is then arranged in front of the dot matrix sensor. The additional incident lighting may be generated by a plurality of light-emitting diodes having different colors or one or more white-light light-emitting diodes.

According to one exemplary embodiment of this variant of the present invention, a first polarizer is arranged between the collimator and one or more light-emitting diodes of the lighting system, and a second polarizer, which is rotated by 90° C. in relation to the first one and has a diameter that corresponds to the incident-light diaphragm and has a central hole (transmitted-light diaphragm), is arranged in the diaphragm plane of a telecentric lens.

However, depending on the embodiment of the present invention, a polarizer is not absolutely necessary for the transmitted-light lighting means if the light source already emits polarized light. This applies, for example, typically to edge emitter laser diodes.

The determination of the particle size distribution for measured diffraction patterns is preferably performed on the basis of response functions for distributions of particles, which are stored in the computing means. The response functions preferably correspond each to distributions of particles of different sizes. The computing means is set up now to determine a particle size distribution belonging to a measured intensity distribution by adapting a weighted superposition of the response functions, The weighting factors for the superposition now correspond directly to the dimensions of the particles. The weighting factors may correspond to both the projection area percentages and the diameters or volumes of the particles.

The advantage of the use of response functions is that device-specific parameters are also taken into account in the response function. Aberrations of the optical system and inhomogeneities of the lighting means can be taken into account with such parameters. Measurement in the Fraunhofer region, which is otherwise necessary to make it possible to describe a diffraction pattern in Fraunhofer approximation can also be avoided hereby. Measurement in the Fraunhofer region requires a great distance from the measuring volume and hence complicated optical systems. However, if the measurement is carried out, by contrast, as is preferred according to the present invention, with shorter focal distances below 55 mm and correspondingly shorter distances, the center of a diffraction pattern is determined sensibly by the distance of the corresponding scattering center from the optical axis. Since the response functions are based on spatial particle distributions and different distances of particles from the optical axis are thus already taken into account, this problem is circumvented.

To set up response functions, aberrations of the optical system of the spectral analyzer or of the second optical measuring system, especially the radial center shift of the spectrum as a consequence of a lateral and/or radial shift of an object in the object space, can be represented as a function of the radial distance from the location of the optical axis on the dot matrix sensor, and the illumination in the object space can be scanned with constant radius. The shifted and weighted diffraction pattern can then be accumulated over the round angle for each radius. A mean dot spread function can be subsequently calculated by integration over the radius or in the entire image field. This dot spread function can then be used instead of the standardized Bessel function for the approximation.

The determination of the response function can be carried out by pure calculation if the optical properties of the system are sufficiently known. It is likewise possible to set up response functions on the basis of model distributions, e.g., by means of suitable templates, which simulate scattering centers of particles of a certain size. However, the two methods can, in particular, be combined with one another. To simulate spatial particle distributions by means of the templates, measurements with templates shifted by different amounts along the optical axis and/or with templates with three-dimensionally distributed scatter centers can be carried out to determine the response functions.

To reduce the amount of calculations needed for determining the particle size distribution, it is favorable, furthermore, if the computing means is set up to determine a diffraction spectrum from the integration of the image brightness over rings around the center of one or more diffraction patterns recorded by the dot matrix sensor of the second optical measuring arrangement. The term diffraction spectrum designates, in the sense of the present invention, the intensity distribution in the radial direction, i.e., the intensity as a function of the radial distance from the center of the diffraction pattern detected by the sensor. The information of the two-dimensional image is thus reduced to a function of a variable, namely, the radius. Based on this diffraction spectrum, adaptation of a calculated spectrum can now be performed, from which the particle size distribution is then derived.

Large particles may distort the result when calculating the particle size distribution from the measurement of the diffraction pattern, because they always generate high-frequency interferences. To minimize such interferences, images that contain excessively large particles can be excluded from the analysis of the diffraction pattern in a very simple manner. In a variant of the present invention, the computing means is set up for this to analyze basic data of the second optical measuring system by Fourier transformation, preferably fast Fourier transformation or an equivalent transformation and to determine the high-frequency component above a frequency threshold value, wherein diffraction patterns for which the intensity of the high-frequency component exceeds another threshold value are sorted out.

The frequency threshold value is not, of course, defined here as a frequency in the sense of a number of vibrations per unit of time. This value pertains rather to the period of the oscillations in the recorded image. When accumulating the data or images not sorted out, it is favorable, furthermore, if the computing means also accumulates the integration times of the sensor and subsequently divides the result by the accumulated integration time.

The present invention will be explained in more detail below on the basis of exemplary embodiments and with reference to the drawings. Identical reference numbers designate identical or corresponding elements. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings in particular, particles with preferably known features are to be measured optically in a particle stream by means of the present invention and combined into clusters or classes. The features of the clusters are determined and, in particular, area distributions are derived. Mass distributions can, in turn, be derived from the area distributions. Process control variables for an in-line regulation of machines arranged upstream of the measuring device according to the present invention, which affect the particle stream and, in particular, generate the particle stream, can be derived from the area, size or mass distributions. For example, the pressure, which is admitted to a nozzle for generating an aerosol, is regulated as a function of the particle size distribution. One task is also to reach the highest possible throughput at only one measuring site and thus to reach a high measuring rate in order for the measuring cycle to be as short as possible. It is also possible to make a prognoses on the basis of changes in the particle size distributions.

The projection areas of particles are detected optically at right angles to the mean velocity vector of a flow containing particles within a transparent measuring volume. Flow parameters may possibly also be calculated and the probability of particle detection can be determined during the measurement.

The particle density differs typically by several orders of magnitudes in case of types of particle streams especially suitable for the present invention, and small particles are, in general, considerably more frequent than large ones.

A defined minimal measuring cross section, within which large particles can essentially also be transported without disturbances, is favorable for a typically broad measuring range of particle diameters between 1 µm and 5 mm. A large depth of field range, which is larger than the measuring range (greater than 5 mm in the example), is therefore also advantageous for an optical inspection according to the present invention.

Two fundamentally different classes of processes are used to measure the projection area of the particles or generally the size thereof. In a first process, the diffraction pattern of the particles is generated at a mostly relatively great measuring distance and then analyzed. The particle stream is lighted for this preferably telecentrically and/or preferably in transmitted light, the diffraction pattern is recorded by a sensor, which is analyzed preferably cylindrically symmetrically and along circles around the center of the diffraction pattern. The radial energy or intensity distribution thus measured is in connection with the theoretically calculated energy or intensity distribution of particles assumed to be circular. This assumption is met in case of small particles in a good approximation.

The diffraction signal of a circular particle can be described in the Fraunhofer region approximation (Fraunhofer diffraction) by a Bessel function of the first type. There are two variants for the signal analysis: First, the use of very fast sensors, which analyze, in principle, only one particle within the measuring volume, or, second, the use of sensors, which analyze the superposition of a plurality of particles. The process or a corresponding device is called spectral analyzer and is used for the present invention as a second optical measuring system.

It is disadvantageous for the practical application that significant measuring errors occur especially in case of large particles. These are generated by deviations in shape from the model of a circular projection area as well as by objects cut at the margin of the image. Furthermore, a color analysis is not possible or is at least difficult for classifying particles of identical area but different colors. A broad-band or multicolor lighting by incident light is favorable for the analysis of color. The different wavelengths used for this would lead to diffraction patterns of different sizes in the spectral range in case of geometrically identical particles in the spectral range, which are superposed to one another in a complex manner. A diffraction measuring process is therefore suitable only conditionally for a differential analysis of a particle stream taking the particle color into account.

Another approach is based on a transmitted light measurement according to the principle of a measuring microscope operating in transmitted light. This process, carried out by the first optical measuring system, is called projection area analyzer. Its advantage is that particles can be separated (segmented) and that a shape analysis can be subsequently performed with contour data. Based on the depth of field requirements, the measurement is especially suitable for relatively large particles (approx. beginning from 100 μm at a depth of field of 5 mm in the example).

The large depth of field range does, in turn, require a small numeric aperture. However, the geometric resolution decreases considerably as a result, so that small particles cannot be resolved or can be revolved only poorly for this reason as well.

The object of the present invention, namely, a broad-band analysis of the size distribution of a particle stream, is consequently accomplished in that a spectral analyzer (the second optical measuring device) and a projection area analyzer (the first optical measuring device) are used in a particle stream at directly adjacent measuring sites or at the same measuring site via beam splitters and can be optionally complemented with additional measuring methods, A telecentric transmitted light source and a telecentric lens with a camera are arranged in an especially advantageous embodiment above a transparent measuring volume, through which a particle stream flows. Short light pulses of a power LED are expanded for this into a telecentric beam, which passes approximately homogeneously through the entire measuring cross section. The particles are then projected with the telecentric lens onto a first dot matrix sensor. The f-number of the lens is preferably selected to be sufficiently high, so that an approximately equal, high-definition imaging with a likewise approximately constant dot spread function is formed in the entire depth of field range. Taking the dot spread function into account, an edge model can be obtained for detection preferably to subpixel accuracy.

The image signal is scanned at a high image repetition rate, preferably at least 10 images per second and subsequently converted with an algorithm with subpixel accuracy, which is coordinated with the dot spread function into contour dots and then segmented into contours. The high computing capacity necessary for this (typically more than 40,000 MIPS) is embodied in terms of hardware especially preferably with an FPGA as part of the computing means according to the present invention. Contours beginning from a certain length are then outputted to a processor (DSP). The problem that particles are imaged only partly at the image margins can be solved exactly by the fact that the touching of the margin by the particles is analyzed and, according to a variant of the present invention the analytical continuation is approximated if necessary. As a result, the DSP is able to process the objects of the incoming images in video real time.

The method can be especially advantageously complemented with a color sensor. A preferably white LED or another, preferably white light source is used for this as a transmitted light source, and the gain of the color channels is balanced such that a homogeneous, uniformly controlled background is obtained in case of missing particles. The transmitted-light measurement thus functions as described above in the monochromatic case. In addition, another, likewise white incident light source is used, which is cycled synchronously with the transmitted light source but has an exposure time that is not necessarily identical to the transmitted light source.

The exposure of the incident light source is advantageously selected to be such that at most 50% and especially preferably 20% of the control is reached on the color sensor in case of a white reference object compared to the control by the transmitted light source. The contour site is affected at most only marginally if at all by a nonlinear gray value characteristic during the contour dot recognition, which is preferably achieved by a convolver.

The hardware-supported preprocessing yields concatenated, attributed contour dots, which can be characterized, among other things, by a characteristic contrast. By concatenating adjacent contour dots, an object list can be generated in real time, which contains the area, circumference and contrast coating (direction-dependent correctly accumulated contrast of the concatenated contour dots) as important object characteristics. The relevant objects are filtered out of this list, and the values contrast coating×circumference>threshold value 1, and projection area>threshold value 2 are used as an indicator. These criteria have the property that distinction can be made between relatively low-contrast, but cloudy dust deposits and clearly delineated particles imaged with relative high definition.

In a variant of the present invention, stationary deposits can be seen by local histograms. The image field is preferably divided for this into geometric zones, and the particles found in the zone over an entire measuring sequence, for example about 1,000 images, including the centers of gravity of these particles, are entered. If a number of objects of equal size with identical center of gravity coordinates occurs in a zone, it is a contamination. The product flow can be switched off in this case and a new teach-in can be carried out, and the affected regions with contaminations are excluded during the subsequent image analysis.

Since the contours of suitable particles with a minimum area are detected by the first processing step, the color signal is subsequently analyzed within the contour. A reduced resolution compared to the contour measurement is usually sufficient for this. The color channel, which is operated with incident light and is therefore more insensitive, can therefore provide exposure longer than the transmitted light channel.

Furthermore, a small diaphragm (e.g., k=50) of the telecentric measuring lens is unfavorable for achieving a high depth of field for the color channel, because the sensitivity is greatly reduced. It is therefore advantageous to form the diaphragm in the form of a polarization filter with a hole on the optical axis and, furthermore, to place a polarizer that is crossed in relation thereto in front of the transmitted light source. As a result, a first aperture is obtained for the transmitted light source (small diaphragm opening), which is determined by the diameter of the hole, and a larger aperture (larger diaphragm opening), which is determined by the diameter of the free part of the polarizer in the diaphragm plane, is obtained for the incident light source. As a result, a larger blur circle is obtained for the color image compared to the transmitted-light arrangement, and the resulting sensitivity of the color sensor improves quadratically with the increase in the effective diameter.

The color image of the sensor is now transmitted in real time into the main memory of a digital signal processor (DSP) together with the contours beginning from a certain length. Regions of interest (ROI) of interesting areas are seen from the contours, and local color images are then calculated in these areas for further analysis.

The color image of the particle within the contour is finally analyzed, a feature vector is generated for each particle and stored in a particle list, from which parameters of particle clusters can finally be estimated by the computing means.

Directly next to the measuring site of the transmitted-light arrangement or by means of beam splitting at the same site, a second measuring channel is arranged according to the diffraction method.

This channel does not operate, unlike in prior-art arrangements, in the Fraunhofer region, but in the diffraction near field (Fresnel approximation) or in the transition range. The arrangement therefore preferably contains measures for radiation formation and masking, especially a pinhole for accurate cross section definition. Another measure, with which high intensities of direct or forward-scattered radiation are prevented from reaching the sensor, is a blind hole in a lens, whereby the direct radiation of the lighting means, i.e., the component of the light not diffracted at particles is focused onto the blind hole and whereby the blind hole is lined with a light-absorbing material. The direct beam of the source is thus absorbed in the blind hole. Diffracted components of the source pass by the blind hole and can thus be detected. For example, chromium dioxide is a suitable light-absorbing material.

The diffraction pattern is imaged onto a cylindrically symmetrical sensor. This is formed by a CMOS or CCD sensor, whose image data are outputted to subpixel accuracy by means of a parametrizable, hardware-supported transformation into polar coordinates. The scan values are azimuthally integrated onto the respective radius, the output signal after the integration corresponds to the signal of a ring sensor, and it is called spectral circular integral. The spectral ring integrals are accumulated over a measuring cycle, and the accumulated ring integral (AKI) is obtained, which is directly related to the accumulated spectra of the particles.

Based on the stochastic spatial distribution of small particles in the measuring volume (there are more than 100,000 per cycle), spectra are generated, which are not imaged identically with the same center as in the Fraunhofer approximation (Fraunhofer), even though they are determined based on the Fresnel approximation.

A special spectral model is therefore advantageously used. It is first assumed for this that all particles would have the same diameter. The superposition of the spectra of all particles in the measuring volume is then calculated, taking into account the spatial distribution thereof, the known light distribution of the laser in the measuring volume and the aberrations of the imaging optical system. The response function or System Response Function SRF=f(R,) of the real system is obtained. The calculation and/or measurement is then repeated for other radii. Known distributions, e.g., velocity variations, may be taken into account if needed. The system is fully calibrated hereby.

Figure 1:
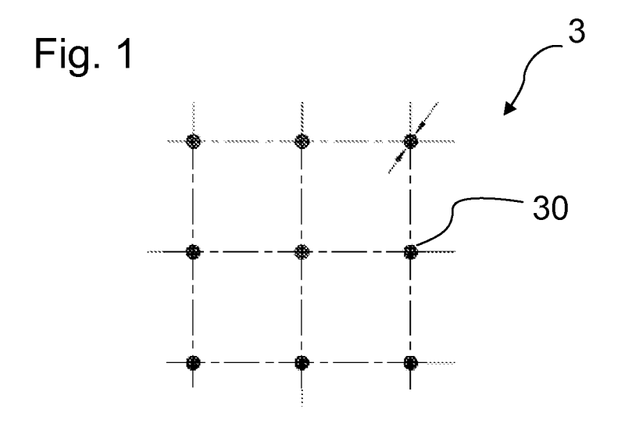
FIG. 1 is a test grid for determining the response function of the second optical measuring system.

The SRF can be determined specifically as follows. A group of circle dots 30 with equal diameter arranged in a grid 3 is entered into the beam path on a target. Such a sample is shown in FIG. 1. For example, the sample may have, as is shown in FIG. 1, a square 3×3 grid of circle dots 30 with a diameter of 50 micrometers (μm).

Figure 2:
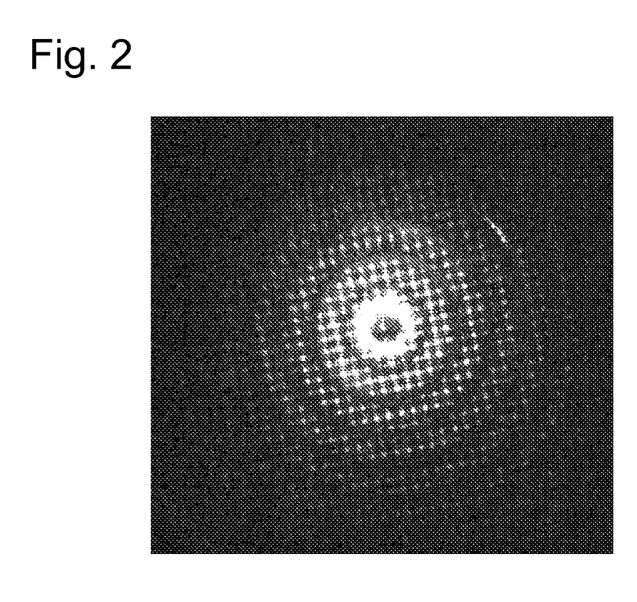
FIG. 2 is a diffraction pattern of the grid shown in FIG. 1, which was recorded by the second optical measuring system.

The recording of the diffraction pattern of grid 3, recorded by the second optical measuring system, is measured with image processing means. Such a diffraction pattern is shown in FIG. 2. The diffraction rings at the individual circle dots 30, to which a grid-like pattern is superposed based on the diffraction at the grid formed by these dots, can be clearly seen.

Grid 3 is typically smaller than the field of view of the sensor. The grid constants or the distance of the next adjacent circle dots 30 may be, for example, 200 μm, wherein the illuminating laser beam has a beam diameter of 4 mm.

An imaging scale β (this is constant in a good approximation) and a small offset of the spectrum in relation to the optical axis, which can be accurately calculated from the position of the dot in the spectrum, are obtained for each shift vector of the central grid dot in relation to the optical axis. Among other things, such an offset would not be noticeable any more during a measurement in the Fraunhofer region. However, a Fraunhofer approximation requires very long focal distances.

Under these measuring conditions, the energy or intensity distribution follows in a good approximation a function derived from the first-order Bessel function. The energy distributions are then accumulated in a weighted manner, and the SRF of a particle distribution with equal diameter (i.e., of particles with a beam diameter of 50 μm in the above-mentioned example) is obtained. Another sample with another diameter can now be used and the diffraction pattern recorded. This operation can be repeated especially for a large number of diameters. A two-dimensional function SRF (R,ω) which fully describes the measuring system and wherein R denotes the particle radius and ω the frequency in the diffraction spectrum, can thus be obtained from these samples. Depending on the knowledge of the optical features of the system, it is also possible to calculate the response functions, or to build up the calculation of response functions on one or more measured diffraction patterns or to balance calculated response functions with measured diffraction spectra.

The spectrum $S(\omega)$ is obtained from the sum of the corresponding response functions, which sum is weighted with the area percentages $c[R]$:

$$S(\omega)=\Sigma c[R]*SRF(R,\omega). \tag{1}$$

To determine the projection area percentages or generally the particle sizes, the inverse problem is now to be solved, i.e., the best possible weighted combination of functions SRF $(R,\omega)$ is to be determined, whose superposition satisfies a certain condition. For example, the response functions can be superposed such that the mean root square error is minimized. The vector $c[R]$ will then describe the area or size distribution being sought. Fredholm's integral equation is solved in this manner numerically. The selection of the radii is arbitrary within broad limits, so that, e.g., logarithmic distributions can be calculated directly. The area distribution thus obtained can be standardized to the total area in the grid (in the example of the grid shown in FIG. 1, the total area is given by $9\times(\pi/4*140$ $\mu m^2=0.138$ $mm^2)$. A measured distribution can, in particular, also be standardized on the basis of an overlap with the distribution determined on the basis of the first optical measuring system.

Figure 3:
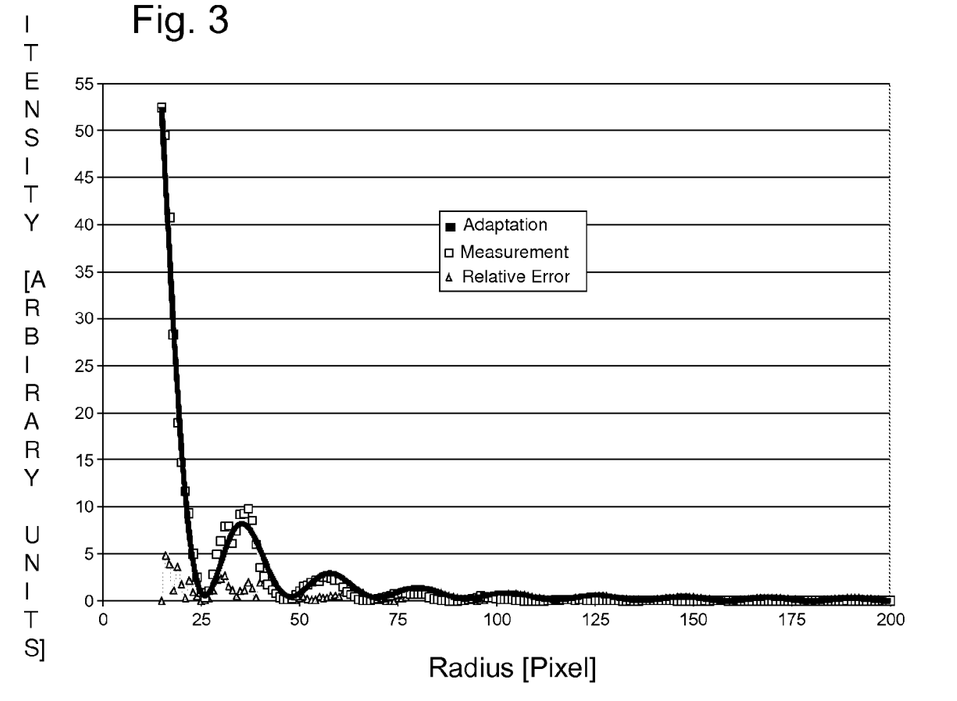
FIG. 3 is a graph showing a spectrum of a particle distribution.
Figure 4:
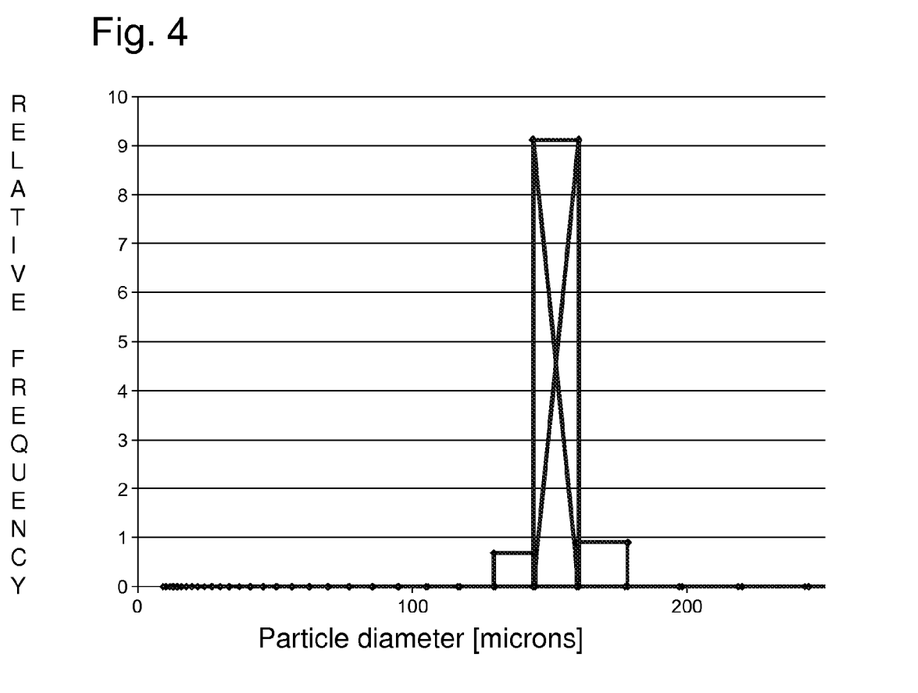
FIG. 4 is a graph showing a particle size distribution determined on the basis of the spectrum.

An example of an adjustment of measured diffraction patterns by means of previously determined response functions is shown in FIGS. 3 and 4. FIG. 3 shows a spectrum determined on the basis of a diffraction pattern, as is shown as an example in FIG. 2, wherein the measured values are shown by open squares. The spectrum is obtained, as was described above, by circular integration around the center of the diffraction pattern. Accordingly, the spectrum describes the intensity or energy as a function of the radius to the center of the diffraction pattern. An adjustment with response functions while minimizing the square error is shown as a solid line. The relative error obtained from the residual deviation of the measured values from the adjustment is additionally shown as well. The corresponding particle size distribution is then calculated on the basis of the adjustment. This is shown in FIG. 4. Accordingly, there is a monodisperse particle size distribution with particle radii of 150 µm in the above example.

Figure 5:
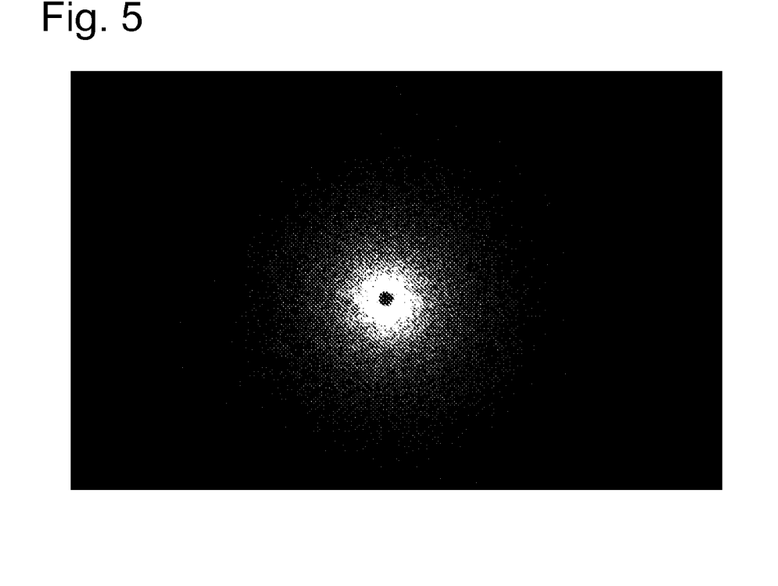
FIG. 5 is a diffraction pattern recorded by the second optical measuring system for a particle stream with a broad-band particle size distribution.

The superposition of the diffraction patterns with different spatial frequencies does, in general, lead to the diffraction rings passing over into each other in case of non-monodisperse or broad-band particle size distributions, and no ring pattern can thus be seen any more. Such an example is shown in FIG. 5. The mean particle size is below 200 µm in this example, but the distribution is such a broad-band distribution that no discrete diffraction rings can be seen any longer. Yet, unambiguous adjustment of response functions to the radial intensity curve can be achieved, so that the particle size distribution can be reconstructed.

Moreover, the spectral analyzer can be corrected concerning an offset by subtracting the accumulated image without particle stream from the accumulated spectral sum.

It is advantageous to know the statistical object distribution for the calculation of the projection area distribution in a medium through which a flow flows for the time-discrete recording of random samples.

The velocity distribution of the particles is not typically homogeneous in a measuring channel through which an essentially laminar flow flows; in particular, the velocity is, in general, lower here at the edges of the channel because of losses due to shocks than in the center. Large particles are also moving more slowly than smaller ones. To take such effects into account, the mean particle distribution can be determined in the measuring volume. A location-dependent velocity measurement can be performed for this at first.

Measurement of the velocities according to the following process is especially advantageous: Two images that follow each other immediately are made in transmitted light by means of the first optical measuring system. Small and large particles are present in the image field. The large particles (e.g., beginning from a diameter of 100 µm) are segmented in both images in the first process steps, and the coordinates of the center and the object contours are determined. A correspondence list of identical objects is then formed from the two images and the image field is divided into a plurality of strips in the transport direction. The mean shift vector is formed for each of the strips and divided by the recording time difference. A lateral frequency distribution, which can also be calculated separately for particles of different sizes, is obtained.

The velocity of the small particles, which are not resolved by the system, can be calculated according to the following process: In a first step, the areas in which large particles were already found are blocked in both images for the determination of the velocity. A cloudy gray value distribution remains, which is transported from the first to the second image in the absence of turbulence. The cross correlation function between the two images is then calculated, and the blocked structures are excluded (it is sufficient to block one of the images, the subsequent standardization prevents errors in calculation).

A mean shift vector is obtained for the class of small particles, for example, small than 100 µm, and this vector can be converted into a mean velocity. There are only low friction losses at the boundary surfaces in this size range, and the variation in velocity is small in the diameter range of up to 100 µm. The measured value can therefore be assumed in a good approximation to be the mean flow velocity.

When calculating size histograms, for example, projection histograms (area distributions) in a particle stream, the throughput per area class is proportional to the particular velocity at the measuring site. The lists of particle features are consequently multiplied by the measured data of the velocity (also location-dependent in case of large particles). In case of small particles, the measured velocity value is multiplied to the distribution measured by the diffraction sensor.

As was said, overlap of the measuring ranges of the two sensors is advantageous, and the information generated here (both sensors yield identical results in an interval) can be used to calibrate the area percentages especially of the diffraction sensor.

The design of the optical measuring arrangement will be described in more detail below.

Figure 6:
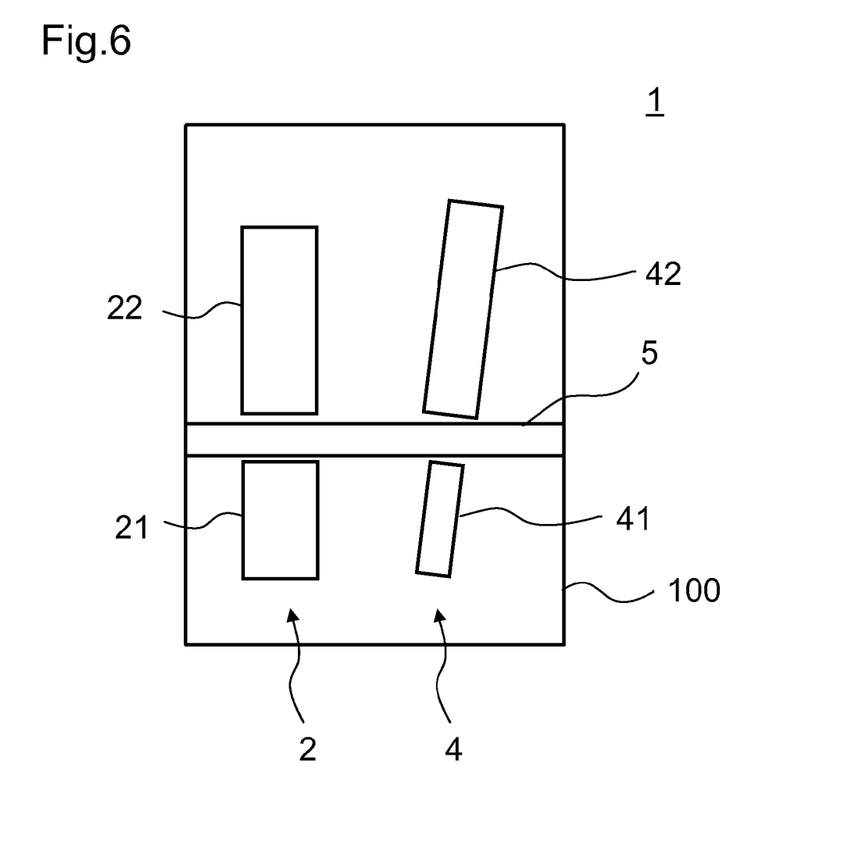
FIG. 6 is a side view of the measuring arrangement.
Figure 7:
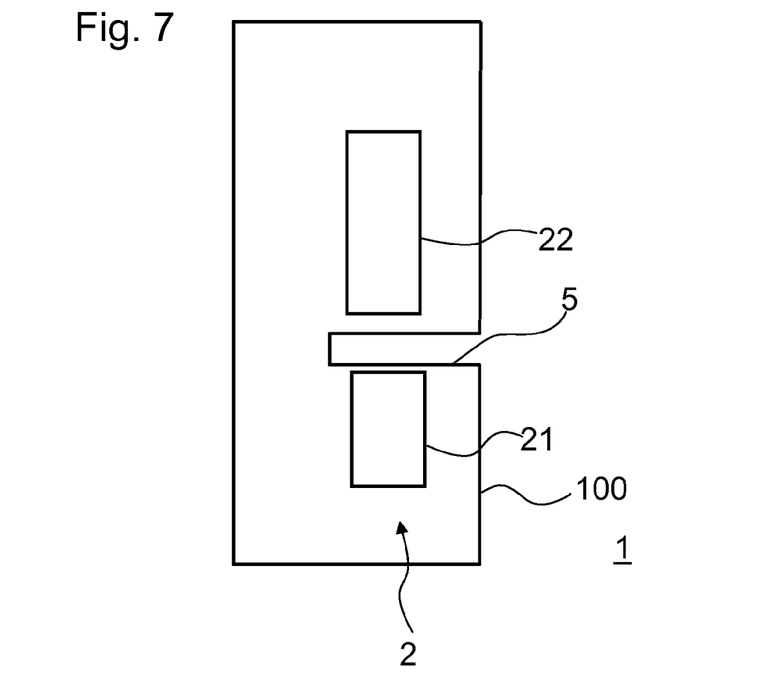
FIG. 7 is a front view of the measuring arrangement as viewed in the direction of the particle stream.

FIG. 6 shows for this a side view of the measuring arrangement and FIG. 7 a front view as viewed in the direction of the particle stream.

Measuring arrangement 1 comprises a housing 100, in which the first optical measuring arrangement 2 and the second optical measuring arrangement 4 are accommodated. The housing has a channel 5, into which a tube carrying the particle stream can be inserted. As can be seen in FIG. 7, the channel is open on the side, so that the measuring arrangement 1 can be attached laterally to such a tube in a simple manner.

The first optical measuring device 2 comprises a lighting means 21 and a camera 22. Lighting means 21 and the camera 22 are arranged opposite each other, so that a transmitted-light arrangement is formed. The camera 22 and lighting means 21 form, in addition, a telecentric measuring system, which is preferably embodied by a parallelized light of the lighting means, on the one hand, and a great depth of field of the camera 22, on the other hand. This is advantageous for not obtaining distance-dependent scale changes, which may distort the calculation of the particle size distribution, during the imaging of projection areas of the particles on the dot matrix sensor of the camera 22.

The second, diffractively measuring optical measuring system 4 is also designed as a transmitted-light arrangement with coherent lighting means 41 and the camera 42. Especially semiconductor lasers may be used as the source for the lighting means 41. However, a white light source is also conceivable for recording wavelength-dependent diffraction spectra with the camera 42. As can be seen from FIG. 6, the optical axis of the second optical measuring system 5 is slightly tilted in relation to the plane at right angles to channel 5 or the direction of flow of the particles, which is defined by the channel Among other things, disturbing interference effects due to back reflections at the window areas of the tube to be inserted are thus prevented from occurring.

Figure 8:
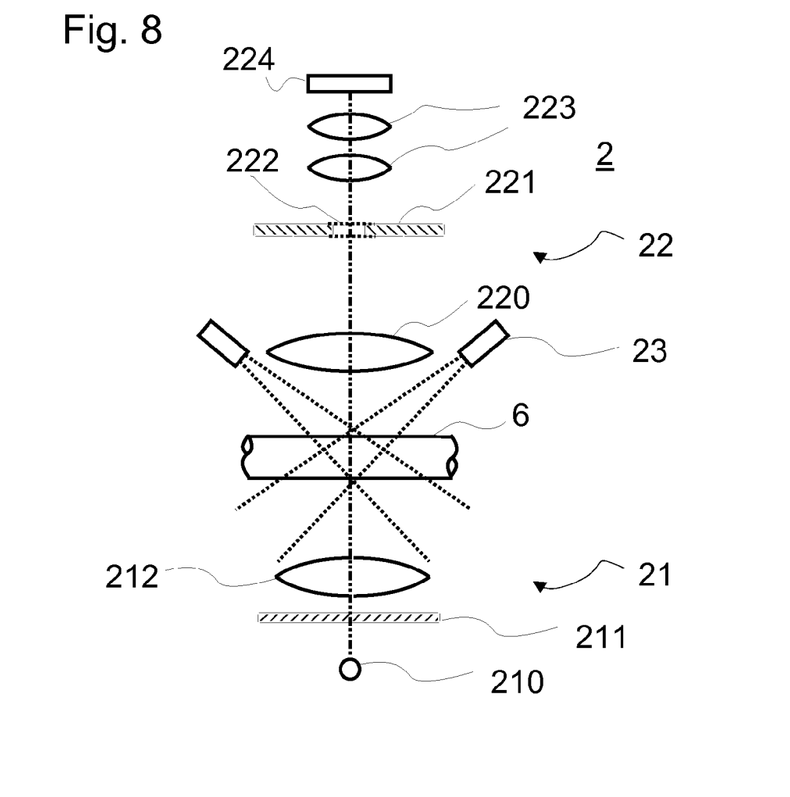
FIG. 8 is a schematic view showing the optical design of the first optical measuring arrangement.

FIG. 8 schematically shows a more detailed design of the first optical measuring system 2. Lighting means 21 comprises a light source, for example, a white light light-emitting diode 210. The light of the light-emitting diode 210 is polarized linearly by means of a polarizer 211, preferably a polarizer film. A condenser lens 212 generates a parallel beam, with which the tube 6 carrying the particle stream is transilluminated. The camera 22 comprises a dot matrix sensor 224 with a telecentric lens arranged in front of it. The lens comprises a condensing lens 220, a diaphragm arranged behind the condensing lens in the beam path and, after the diaphragm, an eyepiece with eyepiece lenses 223 in front of the dot matrix sensor 224. The diaphragm is designed in the form of a polarization filter 221 with a central aperture 222. The polarization filters 221 and 211 are arranged crossed, so that the light of the white light LED 210 passes only through the central aperture 222 of the polarization filter 221 rather than through the polarization filter 221. In relation to the particles lighted in the tube 6 by the white light LED 210, the camera therefore effectively has a diaphragm of the size of the central aperture 222.

An incident-light lighting means is additionally provided. This comprises collimated light sources 23, which light the tube obliquely from the front when viewed from the camera 22. The lighting angle and collimation are selected to be such that the light beams travel past the condensing lens 212. Reflexes of the incident-light lighting means at the condensing lens 212, which reflexes interfere with the transmitted-light measurement, are thus avoided. The light of the incident-light lighting means is unpolarized or is polarized such that the light reflected by the particles in the tube 6 is let through by the polarizer 221. In case of unpolarized light, the components polarized in the blocked direction, i.e., typically half of the light, are, of course, blocked. Yet, the lens for the light of the incident-light lighting means has in this manner an effectively substantially larger diaphragm than for the transmitted-light lighting means. This is meaningful as a lower spatial resolution is sufficient for the incident-light lighting means for color recognition, but a larger signal is obtained.

This principle of a lens diaphragm in the form of a polarizer with aperture can also be advantageously applied to other arrangements and is therefore expressly not limited to the exemplary embodiment of a measurement of particle sizes with two different optical measuring arrangements. Such an arrangement can be used wherever different lightings with different signal strength are present. A fluorescence measurement shall be mentioned as an example. Excitation can be performed here with polarized light and the objects can be imaged with polarized light and a small diaphragm. A substantially larger diaphragm and hence higher sensitivity of the camera are thus available for the weak, unpolarized fluorescence signal. A camera with lighting means as described on the basis of FIG. 8 can also be used for tasks other than the determination of particle size distributions, e.g., generally for image segmenting and image recognition.

Accordingly, a device for lighting and recording objects, especially for contour recognition and object segmentation is provided in another aspect of the present invention, wherein said device comprises a polarized lighting means and a dot matrix sensor with lens, wherein the lens has a diaphragm in the form of a polarizer with a central aperture. The lighting means may be arranged opposite the lens in order to achieve transmitted-light lighting. In addition, as is shown in FIG. 2, one or more incident-light light sources may be provided, which radiate their light collimated and obliquely to the optical axis, so that it travels past the condensing lens of the transmitted-light lighting means.

Figure 9:
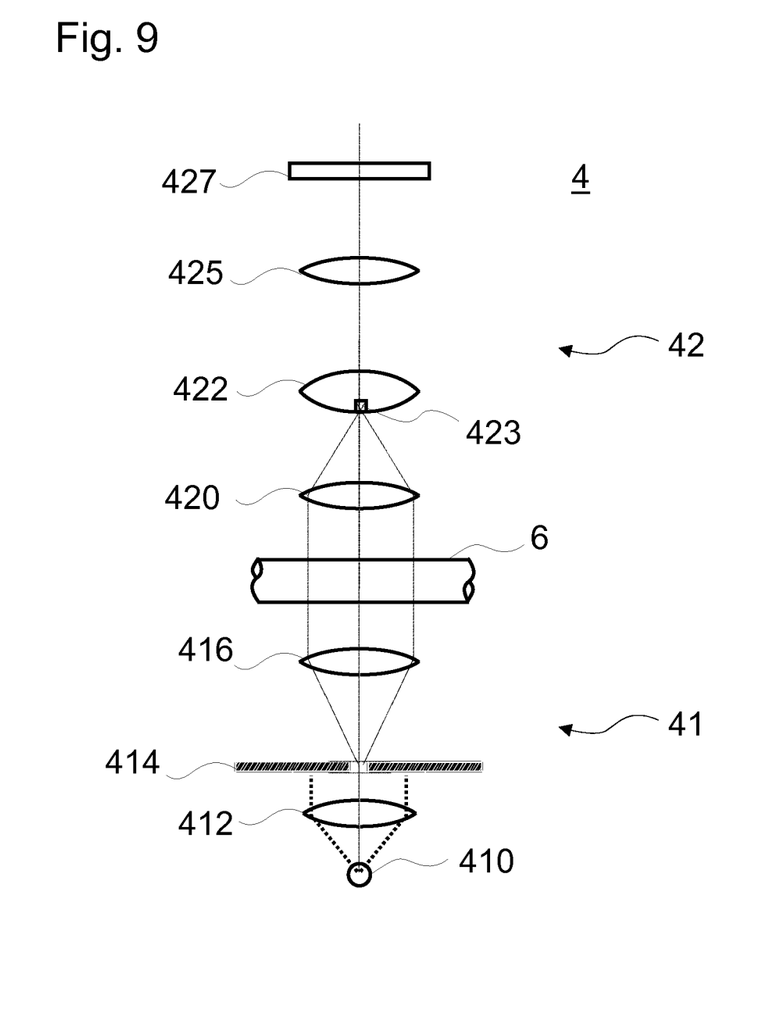
FIG. 9 is a schematic view showing an exemplary embodiment of the design of the second optical measuring arrangement.

FIG. 9 shows an exemplary embodiment of the design of the second optical measuring arrangement 4. The lighting means 41 comprises a laser diode 410 for generating coherent, monochromatic light. A downstream lens 412 is used as a condenser. A collimator 414 with a pinhole is used for a precise beam definition. A punctiform light source is used with this pinhole, and the light passing through is parallelized by means of another condensing lens 416.

Camera 42 comprises a condensing lens 420 as a first optical element facing the particle-carrying tube 6. Another lens 422 is arranged downstream at a distance in the beam path. A blind hole 423, which is lined on all sides with a highly light-absorbing material, for example, $CrO_2$, is located centrally in this lens. A blind hole coated with $CrO_2$ with a diameter smaller than 200 µm and a depth smaller than 250 µm was used in a practical example.

As can be seen on the basis of the beam path drawn by broken line, the direct laser radiation, which passes through the tube 6 in a straight line, without being diffracted, is focused by the condensing lens 420 exactly onto the blind hole 423. The diffracted components travel, by contrast, laterally past the blind hole 423. The diffraction pattern is then focused by means of another lens 425 onto the dot matrix sensor 427.

The present invention, as it was described above, is suitable for a plurality of applications, because broad-band particle size distributions may occur in many technical areas. One application is motive power engineering or environmental technology, here, e.g., for the very rapid analysis of soot or exhaust gas particles of engines. The present invention can also be used for the analysis of particle-containing emissions of smokestacks. Particles are formed in many reactions in the chemical and pharmaceutical industries, e.g., during the precipitation of substances, in polymer synthesis, when producing granular materials, and also in combustion operations, as well as detecting and classifying particulate natural substances. The present invention can be used for rapid testing and further also for process control here as well. For example, the reaction temperature in chemical processes can also be controlled on the basis of the detected particle size. The device can be used in the pharmaceutical as well as chemical industries to check the particle size distributions of particulate precursors.

Furthermore, filtration operations, e.g., generally in building engineering, for example, for clean rooms, or in air conditioning, can also be monitored.

While specific embodiments of the invention have been described in detail to illustrate the application of the principles of the invention, it will be understood that the invention may be embodied otherwise without departing from such principles.

The invention claimed is:

1. A device for determining particle sizes of particle streams through a measuring volume, the device comprising:
    an optical measuring arrangement detecting the measuring volume; and
    a computing means connected to the optical measuring arrangement, wherein
    the optical measuring arrangement comprises a first optical measuring system with a first dot matrix sensor and with a lighting means, wherein
    the lighting means transilluminates the measuring volume and the first dot matrix sensor and the lighting means form a transmitted-light arrangement, and wherein
    the computing means determines projection areas of particles within the transilluminated measuring volume from image data of the first dot matrix sensor,
and wherein
    the optical measuring arrangement comprises a second optical measuring system with a second dot matrix sensor for detecting a diffraction pattern of the particles, and wherein
    the computing means determines a size distribution of the particles in the measuring volume on the basis of the projection areas and the diffraction pattern, wherein
    the computing means determines the size distribution from particle sizes determined on the basis of the projection areas, and the computing means determines the particle size on the basis of the detected diffraction pattern, wherein aberrations of an optical system of the second optical measuring system, including a radial center shift of a spectrum as a consequence of one or more of a lateral and a radial shift of an object in an object space, is represented on the second dot matrix sensor as a function of a radial distance from a location of an optical axis and illumination in the object space is scanned with constant radius, wherein a shifted and weighted diffraction pattern is accumulated over a round angle, and wherein a mean dot spread function is calculated by integration over the radius via said computing means.

2. A device in accordance with claim 1, wherein the second optical measuring system is designed as a transmitted-light arrangement.

3. A device in accordance with claim 1, wherein the first and second optical measuring systems have different image magnifications, wherein the second, diffractive optical measuring system has an imaging scale that is at least twice an imaging scale of the first optical measuring system.

4. A device in accordance with claim 1, wherein the first optical measuring system records at least two images one after another, wherein the computing means calculates the change in location in the two images for particles with a size of the area projection above an area threshold value and determines a velocity distribution as a function of the distance difference of the particle location and the particle size, and wherein the computing means, while excluding particles with a size of the area projection above an area threshold value, correlates the remaining gray scale value distribution between the two images, to determine the corresponding shift vector and to calculate a mean velocity for small particles and to compose from the two measurements a uniform velocity model, and determines a data structure with particle histograms and location- and size-dependent measured velocity data or a particle size histogram corrected with the detection probability, in the form of a projection area histogram.

5. A device in accordance with claim 1, wherein the first optical measuring system comprises an additional multicolor, white incident-light lighting means, wherein the dot matrix sensor of the first optical measuring system is designed as a color sensor.

6. A device in accordance with claim 5, wherein the computing means assigns the color information to particles to calculate a particle size distribution, which contains the particle color or a parameter assigned to the color as an additional attribute.

7. A device in accordance with claim 5, wherein the computing means determine contours belonging to particles and performs a color analysis selectively within the contours belonging to the particles.

8. A device in accordance with claim 1, wherein the lighting means, which forms a transmitted-light arrangement with the sensor, is designed as a linearly polarized lighting means, wherein a lens with a diaphragm, which said lens is designed in the form of a polarization filter arranged crossed in relation to the polarization plane of the light with an aperture opening arranged therein, is arranged in front of the dot matrix sensor of the first optical measuring arrangement.

9. A device in accordance with claim 1, wherein the computing means determines a diffraction spectrum from integrations of the brightness over rings around the center of one or more diffraction patterns recorded by the dot matrix sensor of the second optical measuring arrangement.

10. A device in accordance with claim 1, wherein the computing means analyzes basic data of the second optical measuring system by Fourier transformation, fast Fourier transformation or an equivalent transformation, and determines a high-frequency component above a threshold value, wherein diffraction patterns for which the intensity of the high-frequency component exceeds another threshold value are sorted out.

11. A device in accordance with claim 1, wherein response functions for distributions of particles are stored in the computing means, wherein the response functions correspond each to distributions of particles of different sizes, and wherein the computing means determines a particle size distribution belonging to a measured intensity distribution by adjustment of a weight superposition of the response function.

12. A device in accordance with claim 1, wherein a lens with a focal distance shorter than 50 mm is arranged in front of the dot matrix sensor of the second optical measuring system.

13. A device in accordance with claim 1, wherein a lens, in which a blind hole is formed, which is lined with a light-absorbing material and onto which the direct light of the light source not diffracted at particles is focused, is arranged in front of the dot matrix sensor of the second optical measuring system.

14. A process for determining particle size distributions of particle streams, the process comprising the steps of:
a measuring volume is transilluminated with a lighting means by means of a first telecentric optical measuring system;
the transmitted-light signal is detected by a first dot matrix sensor of the first optical measuring system;
projection areas of particles are determined by means of a computing device on the basis of the transmitted-light signal;
a diffraction pattern of the particles is detected by means of a second dot matrix system of a second optical measuring system;
size distribution is determined by means of the computing means from particle sizes determined in the basis of the projection areas and from particle sizes determined on the basis of the diffraction pattern, wherein aberrations of the optical system of the second optical measuring system, including a radial center shift of the spectrum as a consequence of a lateral and/or radial shift of an object in the object space, is represented on the dot matrix sensor as a function of the radial distance from the location of the optical axis and the illumination in the object space is scanned with constant radius, wherein the shifted and weighted diffraction pattern is accumulated over the round angle, and wherein a mean dot spread function is calculated by integration over the radius.

15. A process in accordance with claim 14, wherein the size distribution determined on the basis of the diffraction pattern is calibrated by the computing means by means of an area of the size distribution determined on the basis of the projection areas, which said area overlaps with the size distribution.

16. A process in accordance with claim 14, wherein to set up a particle size distribution, a plurality of images are recorded by the two dot matrix sensors.

17. A process in accordance with claim 14, wherein to determine the projection areas of particles, contour dots are determined to subpixel accuracy and then segmented into contours.

18. A device for determining particle sizes of particle streams through a measuring volume, the device comprising:
an optical measuring arrangement comprising a first telecentric optical measuring system with a first dot matrix sensor and with a lighting means wherein the lighting means transilluminates the measuring volume and the first dot matrix sensor and the lighting means form a transmitted-light arrangement and a second optical measuring system with a second dot matrix sensor for detecting a diffraction pattern of the particles; and a computing means connected to the optical measuring arrangement, wherein:

the computing means determines projection areas of particles within the transilluminated measuring volume from the image data of the first dot matrix sensor;

the computing means determines a size distribution of the particles in the measuring volume on the basis of the projection areas and the diffraction pattern;

the computing means forms a size distribution from particle sizes determined on the basis of the projection areas and particle size determined on the basis of the diffraction pattern;

aberrations of the second optical measuring system, including a radial center shift of a spectrum as a consequence of one or more of a lateral shift and a radial shift of an object in an object space, is represented on the second dot matrix sensor as a function of a radial distance from a location of an optical axis and illumination in the object space is scanned with constant radius, wherein a shifted and weighted diffraction pattern is accumulated over around angle, and wherein a mean dot spread function is calculated by integration over the radius via said computing means.

19. A device in accordance with claim 18, wherein:

the second optical measuring system is designed as a transmitted-light arrangement; and the first and second optical measuring systems have different image magnifications;

the second optical measuring system has an imaging scale that is at least twice an imaging scale of the first optical measuring system;

the first optical measuring system records at least two images one after another;

the computing means calculates the change in location in the two images for particles with a size of the area projection above an area threshold value and determines a velocity distribution as a function of the distance difference of the particle location and the particle size; and the computing means, while excluding particles with a size of the area projection above an area threshold value, correlates a remaining gray scale value distribution between the two images and determines the corresponding shift vector and calculates a mean velocity for small particles and to compose from the two measurements a uniform velocity model, and determines a data structure with particle histograms and location- and size-dependent measured velocity data or a particle size histogram corrected with the detection probability, in the form of a projection area histogram.

* * * * *